United States Patent
Nadezhdinskii et al.

(10) Patent No.: US 7,535,006 B2
(45) Date of Patent: May 19, 2009

(54) GASEOUS URANIUM HEXAFLURIDE ISOTOPE MEASUREMENT BY DIODE LASER SPECTROSCOPY

(75) Inventors: Alexander I. Nadezhdinskii, Moscow (RU); Yakov Ponurovskii, Moscow (RU); Steven P. Kadner, Albuquerque, NM (US)

(73) Assignee: Canberra Albuquerque, Inc., Albuquerque, NM (US)

( * ) Notice: Subject to any disclaimer, the term of this patent is extended or adjusted under 35 U.S.C. 154(b) by 0 days.

(21) Appl. No.: 10/457,646

(22) Filed: Jun. 9, 2003

(65) Prior Publication Data
US 2004/0245470 A1 Dec. 9, 2004

(51) Int. Cl.
*G01N 21/61* (2006.01)
(52) U.S. Cl. ...................................... 250/343
(58) Field of Classification Search .................. 250/343
See application file for complete search history.

(56) References Cited

U.S. PATENT DOCUMENTS

| | | | |
|---|---|---|---|
| 4,734,177 A * | 3/1988 | Robinson et al. | 204/157.2 |
| 5,448,071 A * | 9/1995 | McCaul et al. | 250/343 |
| 5,543,621 A * | 8/1996 | Sauke et al. | 250/339.03 |
| 5,550,636 A * | 8/1996 | Hagans et al. | 356/437 |
| 6,421,120 B1 * | 7/2002 | Wildnauer | 356/243.1 |

OTHER PUBLICATIONS

Fried et al. Versatile integrated tunable diode laser system for high precision: application for ambient measurements of OCS, Applied Optics, vol. 30, No. 15 (May 1991), pp. 1916-1932.*
Anklam et al. Uranium AVLIS Vaporizer Development, SPIE vol. 1859 (1993), pp. 277-286.*
Fried, et al Versatile integrated tunable diode laser system for high precision: application for ambient measurements of OCS, Applied Optics, vol. 30, No. 15 (May 1991) pp. 1916-1932.
Anklam, et al. Uranium AVLIS Vaporizer Development, SPIE vol. 1859 (1993), pp. 277-286.
McDowell, R.S., L.B.Asprey, R.T. Paine, Vibrational spectrum and force field of uranium hexafluoride, J. of Chemical Physics, vol. 61, No. 9, 1974.

* cited by examiner

*Primary Examiner*—David P Porta
*Assistant Examiner*—Shun Lee
(74) *Attorney, Agent, or Firm*—David W. Carstens; Carstens & Cahoon, LLP

(57) ABSTRACT

A device and method for measuring the relative amounts of $^{235}U$ and $^{238}U$ in the gaseous phase of $UF_6$ using tunable diode laser spectroscopy (TDLS). The invention is a faster, more accurate method for making such measurement. The improved method involves using methane ($CH_4$) or acetylene ($C_2H_2$) as a calibration gas, and using a Fabry-Perot interferometer to calibrate the laser frequency, to determine the relative amounts of $^{235}U$ and $^{238}U$ in $UF_6$ gas within ±0.27% accuracy, for example 7.00%±0.27%. The sample time required for such measurement is about one second.

10 Claims, 13 Drawing Sheets

US 7,535,006 B2

GASEOUS URANIUM HEXAFLURIDE ISOTOPE MEASUREMENT BY DIODE LASER SPECTROSCOPY

BACKGROUND OF THE INVENTION

1. Technical Field

The invention relates to the field of measuring the relative amount of the two isotopes of uranium hexafluoride. Specifically, the invention is an improved apparatus and method to quickly and accurately measure the ratio of the two isotopes of uranium hexafluoride in the gaseous phase using tunable diode laser spectroscopy (TDLS).

2. Description of Related Art

Uranium is found naturally as two isotopes: $^{235}U$ and $^{238}U$. Uranium is frequently used in the atomic energy sector. Naturally occurring uranium has a $^{238}U$ composition of 0.7%. Depleted uranium has a $^{238}U$ composition of about 0.2%. To be used in the atomic energy industry, uranium needs to be enriched to about 5.0% of $^{238}U$. Uranium for nuclear ammunitions needs to be enriched more than 20%.

The molecule uranium hexafluoride, $UF_6$, is the single known gaseous uranium molecule used in the field of nuclear energy and has been of significant interest over the last five decades in the separation of uranium isotopes by laser, the separation of $^{235}U$ from its only other stable isotope $^{238}U$ and from other chemical species. Isolating $^{235}U$ from 238U, and from other chemical species, is known as enrichment. Monitoring the relative amounts of $^{238}U$ and $^{235}U$ is important during the enrichment process and during periodic verification of stored uranium hexafluoride. For example, as of the year 2000, over 700 million kilograms of depleted uranium hexafluoride ($DUF_6$), containing 475 million kilograms of uranium, have been generated by the U.S. government. Other sources of $UF_6$ exist.

The main advantage of optical, non-destructive methods of detection, such as TDLS, is the possibility of non-contact isotopic measurement combined with real-time data processing. Another benefit is its high selectivity as different molecules and isotopes have different spectra. These spectra vary with temperature and physical phase.

Currently, there are two types of methods to measure individual gas samples: destructive and non-destructive. The destructive method involves collecting samples in special gas containers and processing these samples through a mass spectrometer. The accuracy of this method is about 1% relative. This method is relatively expensive. A mass spectrometer costs on the order of one million U.S. dollars. Each sample is relatively expensive to gather and process. This method is also very slow: each sample can take up to one hour to process.

There are two non-destructive methods to measure uranium hexafluoride. One method uses $^{241}Am$ as a source of 60 keV gamma-radiation and a low resolution NaI(TI) detector for the measurement of $^{235}U$ and $^{238}U$ by detecting the 60 keV and 186 keV gamma radiation, the last is specific only for $^{235}U$. The content of $^{235}U$ is calculated from the ratio of the two measurements. The other method for the measurement of $^{235}U$ at low pressure uses $^{57}Co$ as a source of 122 keV gamma-radiation.

Both of these methods have a low accuracy, about 20%, for example, 7%±20%. In the industry, these methods have been used to determine if samples of uranium are either greater than or less than 20% enriched with $^{235}U$. However, these methods are useless to distinguish between naturally occurring uranium, having a 0.7% composition of $^{235}U$, and depleted uranium, having a 0.2% composition of $^{235}U$. In these methods, special care is required to differentiate the measurement of the uranium in the gaseous phase from that of the uranium that deposits on the walls of the sample container.

Mid infrared diode laser spectroscopy (IR-DLS) could be applied to the measurement of the uranium isotope concentration in low pressure gaseous $UF_6$. Uranium hexafluoride has many absorption bands located in the mid and far infrared regions of its vibrational energy spectrum. Specifically, the $UF_6$ molecule has six normal vibrational modes: $v_1$=667 cm$^{-1}$, $v_2$=534 cm$^{-1}$, $v_3$=626 cm$^{-1}$, $v_4$=186 cm$^{-1}$, $v_5$=200 cm$^{-1}$, and $v_6$=143 cm$^{-1}$. For TDLS, the most suitable absorption band is the combination ro-vibration band $v_1+v_3$ near 7.8 µm because it has a relatively strong absorption in this region of the spectrum. This band has an unresolved PQR structure corresponding to changes in angular momentum J during transition (P: ΔJ=−1, R: ΔJ=+1, Q: ΔJ=0). Normally, it is impossible to resolve individual ro-vibration lines because of their high density and only their broad PQR structure can be observed. The position of the Q-branch in the center of the band is shifted for different uranium isotopes. This shift can easily be detected by using high-resolution TDLS thus making it possible to measure the concentration of each isotope in the gas. A gas sample with an optical path that is 10 cm long is sufficient to detect a reliable measurement.

It would be ideal to have a device and method to quickly and accurately detect the relative amounts of $^{235}U$ and $^{238}U$ in a gaseous sample. Further, it would be beneficial to have a device that is capable of recording and analyzing such measurements automatically. Further, it would be beneficial to have a device that required only reference gases instead of a sample of known $^{235}U$ activity as a calibration for measurement. Further, it would be ideal to have a device that is relatively inexpensive and portable to make measurements. Finally, it would be ideal to have a device that could take advantage of the recently discovered benefits associated with TDLS.

SUMMARY OF THE INVENTION

This invention is a device and method to quickly measure the ratio of the two isotopes of uranium in the $UF_6$ molecule in the gaseous state with high enough accuracy to distinguish various grades or concentrations of uranium, from strongly enriched or weapon grade uranium to the naturally occurring uranium. Each measurement of the ratio of $^{238}U$ to $^{235}U$ can be performed in about one second with an accuracy of ±0.2%, for example, 7% $^{235}U$±0.2%. Each measurement may be detected, calculated and recorded on a computer using a combination of hardware and software. Each measurement may be taken with a device that is relatively inexpensive and portable. Measurements are taken with reference to methane and acetylene instead of the traditional sample of known concentration of uranium hexafluoride gas.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 5A shows the absorption signals of the three instrument channels: an empty analytic cell, a methane gas sample in one calibration channel, and the transmission through a Ge Fabry-Perot interferometer in one calibration channel. FIG. 5B shows the absorption spectrum of methane gas.

Figure 1A:
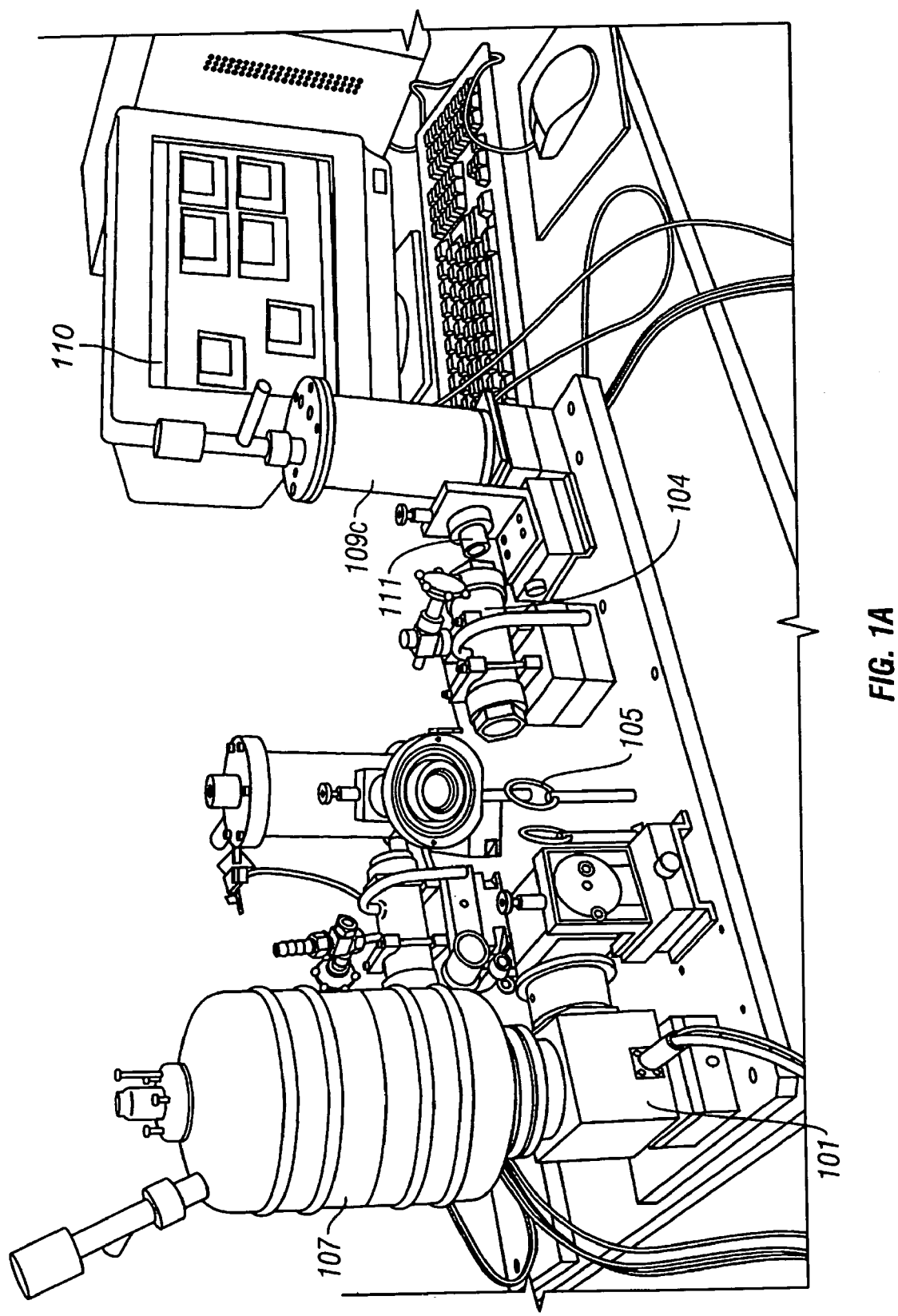
FIG. 1A is a photograph of one embodiment of the apparatus of the invention.

Where used in the various figures of the drawing, the same numerals designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

DETAILED DESCRIPTION

The proposed invention comprises an instrument to quickly and accurately measure the relative amounts of $^{235}U$ and $^{238}U$ in a sample containing $UF_6$ gas.

Instrumentation

The analysis of the $^{235}UF_6/^{238}UF_6$ isotopic ratio by diode lasers (DL) is based upon the principles of high-resolution absorption molecular infrared (IR) spectroscopy. Monochromatic (single-mode) DL's are tunable in a controlled mode and can record the absorption bands of different isotopes of a molecule.

FIG. 1A is a photograph of one embodiment of the invention apparatus. From left to right in FIG. 1A, a cryostat 107 cools a diode laser 100. Two light splitters 105 deflect the emissions from the diode laser 100 to two photo diode detectors 109B and 109C. The emissions from the diode are collimated into parallel a beam laser, before passing through a sample cell 104 and through a lens 111; the lens focuses the laser onto the photodetector 109A. The diode laser is attached to a thermal stabilizer 101. A computer 110 is attached to the apparatus to record the signals from the instruments.

Figure 1B:
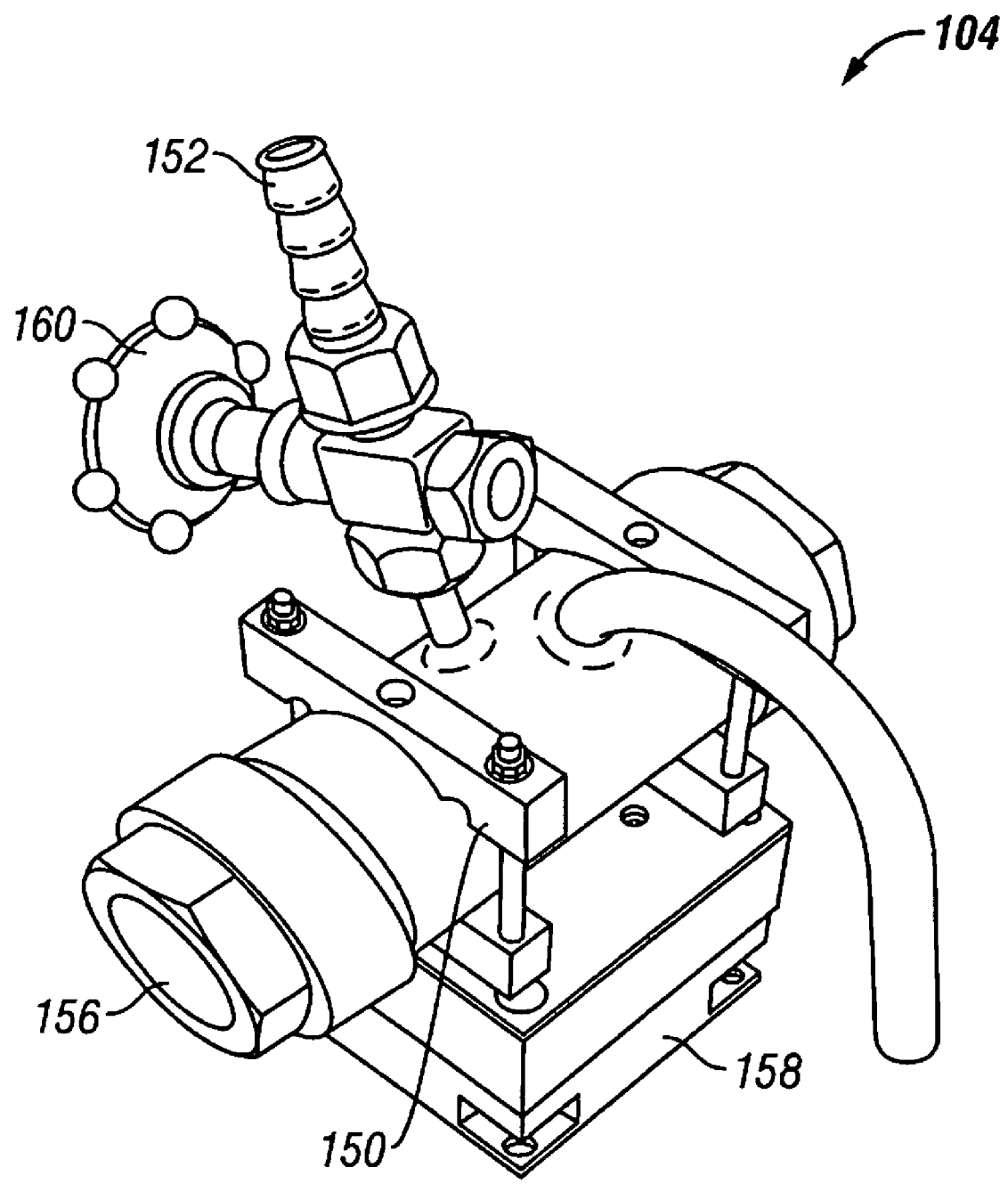
FIG. 1B is a photograph of one embodiment of the optical sample chamber, channel or cell.

FIG. 1B is a photograph of one embodiment of a sample cell or channel 104 shown in FIG. 1A. In this embodiment, the cell 104 is made of stainless steel. The emissions from the DL pass through the cell using a window 156 on each end of the sample cell 104. In one embodiment, the cell window 156 is made of $BaF_2$. This material is transparent in the mid-IR spectral range and does not interact with $UF_6$. $UF_6$ gas under investigation is introduced into the sample cell 104 through a valve 152 controlled by a valve handle 160. The sample cell 104 is attached to a stabilizing base 158 by two u-shaped brackets 150. The description of the embodiment shown in FIG. 1B is shown by way of illustration only and is not meant to limit the scope of the invention.

Figure 2:
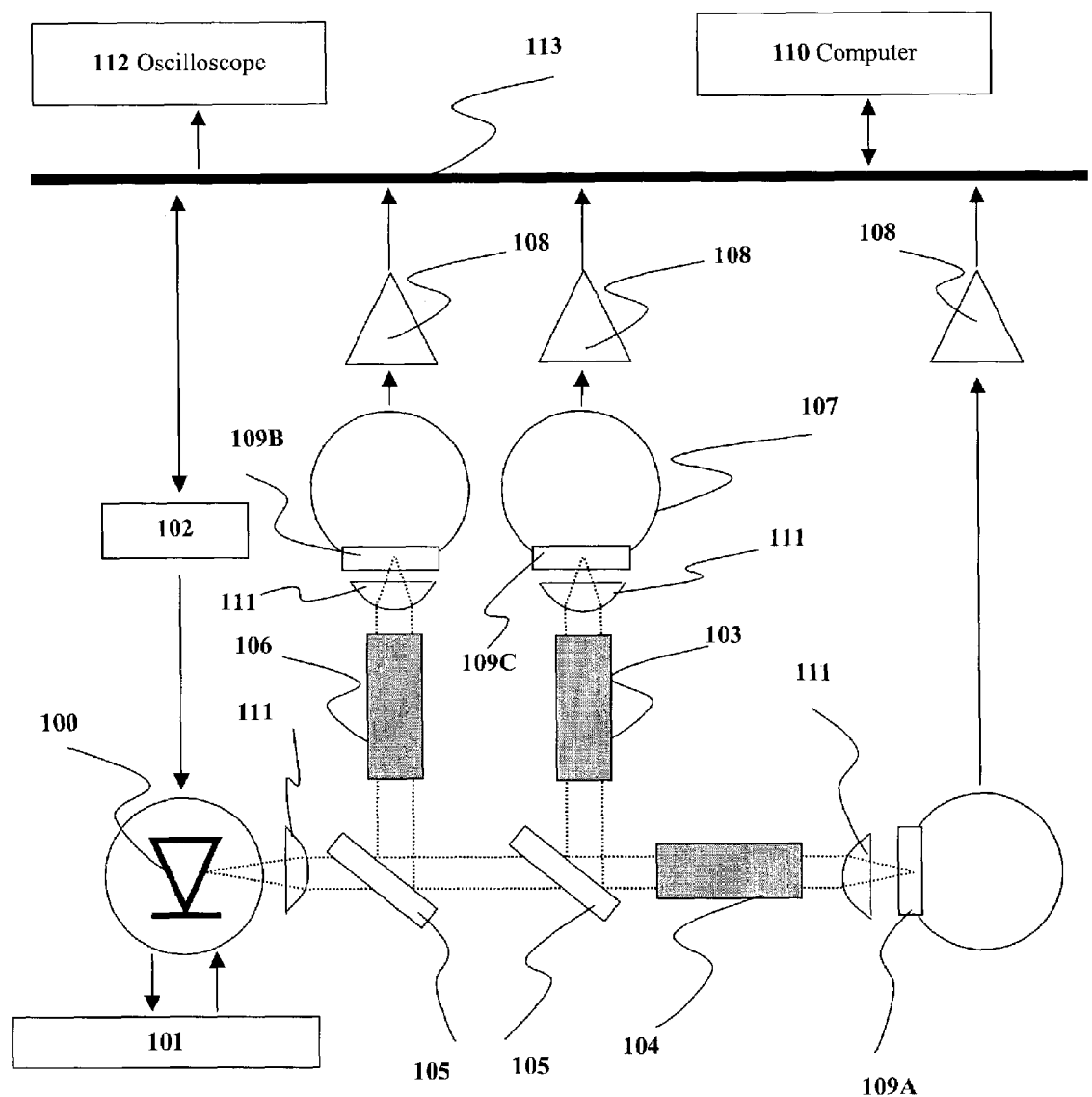
FIG. 2 is a schematic representation of the optical scheme of the invention.

FIG. 2 is a schematic of one embodiment of the invention analogous to the embodiment shown in FIG. 1A. The schematic represents a high-resolution three-channel IR spectrometer based on a diode laser emitting in the mid-IR spectral range ($\lambda$ is about 7.8 μm).

Referring to FIG. 2, the diode laser 100 is installed in a cryostat cooled with liquid nitrogen. The DL frequency depends on its temperature. The temperature of the DL is stabilized using a thermal stabilizer 101, which may contain a heater and a temperature sensor, such as a thermo diode. The DL radiation is collimated into parallel beams by a lens 111 installed in front of the DL 100. Light splitters 105 form three instruments channels. These light or radiation splitters 105, and all spherical lenses 111 are ideally made of $BaF_2$.

In each cell or channel 103, 104 and 106, a lens 111 focuses the laser radiation onto the sensitive area of the photo-detectors or photodiodes 109A, 109B and 109C composed of HgCdTe installed in cryostats 107 cooled with liquid nitrogen.

The analytical channel or cell 104 contains the $UF_6$ gas mixture to be measured. Two reference channels 103 and 106 are used for the DL frequency calibration (see below). In one reference channel 103, a reference gas such as methane or acetylene ($CH_4$ or $C_2H_2$) provides an absorption line to calibrate the DL frequency. The curve representing the DL frequency may be obtained using a Ge Fabry-Perot etalon installed in the other reference channel or cell 106. During the operation of the system, a reference spectral line taken from the first reference channel or cell 103 for the purpose of stabilizing the system and enabling an accurate measurement (see below).

With reference to FIG. 2, signals from the photo diodes 109A, 109B and 109C are amplified by specially developed preamplifiers 108 and recorded by the signal processing board 113 (see below) attached to the computer 110. The computer 110 controls the system. The computer 110 together with current supply 102 generates laser excitation current pulses of special shape, stabilizes the DL temperature through the thermal stabilizer 101, and records the signals from three photo detectors or photo diodes 109. Optionally, an oscilloscope 112 may be attached to the signal processing board 113.

Figure 3:
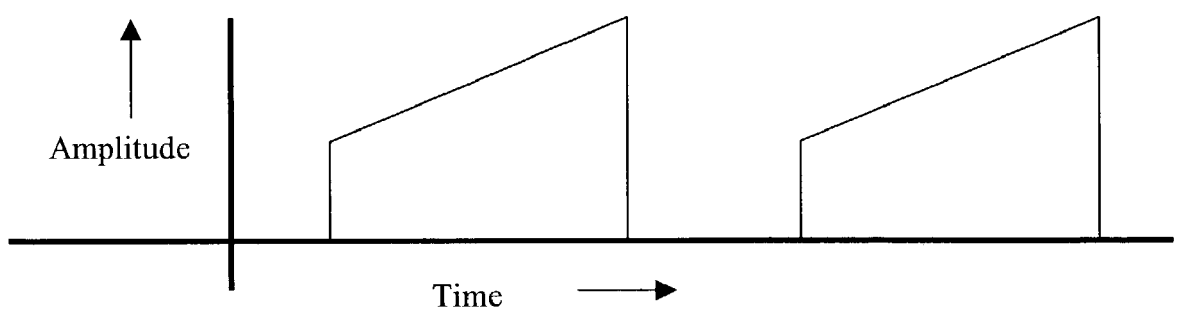
FIG. 3 is a diagram showing the shape of the electric power supplied to the diode laser.

The diode laser emits radiation at a wavelength of $\lambda$ approximately equal to 7.68 μm. It is mounted on a cold copper conductor that is placed in a cryostat 107 that is cooled by liquid nitrogen to $-195.8°$ C. (77.2 deg. K). The DL radiates at a power of approximately 300 μWatts. Referring to FIG. 3, electric power or current is pulsed in a trapezoidal fashion with a mean value of excitation current during the pulse of approximately 300 mA with a pulse length from 4-10 ms at a repetition frequency of about 40 Hz.

With reference to FIG. 2, the thermal stabilizer 101 should operate under proportional-plus-integral (PI) control to ensure that the long-term laser temperature is stable on the order of $5 \times 10^{-3}$ deg. K in any point of the temperature operating range of interest, from 79 deg. K to 115 deg. K. Temperature change provides DL frequency changing of approximately 40 $cm^{-1}$ over the above-mentioned temperature range. Fine-tuning of the DL frequency takes place during a pumping current pulse because of the refractive index changing of the laser's active region with current. Using the absorption lines of a calibration gas as a temperature sensor, the long-term stability of the DL frequency can be maintained at a level better than $2 \times 10^{-4}$ $cm^{-1}$. This stability corresponds to a temperature stability on the same order magnitude, $2 \times 10^{-4}$ deg. K. Methane ($CH_4$) and acetylene ($C_2H_2$) are examples of a calibration gas.

The channel for the reference gas 103 in FIG. 2 is required to perform an absolute frequency scale calibration of recorded spectra. Isolated strong absorption lines of the methane and acetylene in spectral range under consideration may be used to achieve an absolute laser frequency calibration. In one embodiment, the reference gas is held in an optic cell with a length L of 5 cm under a pressure P of 1.5-5.0 Torr.

Referring to FIG. 2, the reference channel 106 is used to determine the frequency-tuning curve of the diode laser. In one embodiment, the reference channel 106 contains a Fabry-Perot interferometer with a free dispersion range of 0.095 $cm^{-1}$. For the purpose of frequency tuning, the values of the centers of the absorption maxima of the Fabry-Perot interference fringes are used. The final stage is an absolute fixing of the frequency scale by absorption lines of a calibration gas. The error in determining the center of the line in any spectral region of the operating mode (the mode length of $\Delta v$ being approximately equal to 3.5 $cm^{-1}$) is less than $2 \times 10^{-4}$ $cm^{-1}$ after completing the linearization and frequency fixing procedures.

Referring to FIG. 2, the analytical channel 104 is designated to carry out routine measurements of the $UF_6$ concentration and the value of the $^{235}UF_6/^{238}UF_6$ isotopic ratio in an unknown gas sample. One embodiment of the analytical channel is an optical cell 10 cm in length.

Referring to FIG. 2, for optimum results, the analytic cell 104 should be preliminarily passivated by adding a gas containing fluorine ($F_2$) and uranium hexafluoride into the cell and leaving the cell for several days. Passivation of the cell 104 is necessary to remove any trace amounts of $UF_6$ before a sample is introduced into the cell. The passivation procedure may result in some slight cloudiness of the windows, probably, due to the deposition of some nonvolatile products of passivation such as $UF_2O_2$.

The preferred embodiment of the analytic cell 104 has a nitrogen trap for gas sample freezing and pressure gauges. The freezing of gas samples in the nitrogen trap allows for the $UF_6$ pressure to be varied in the cell from 0.5 to 150 Torr. In one embodiment, the cell is equipped with a pin made of stainless steel, which may be placed into liquid nitrogen. Because of the passivation procedure, even if there are some trace amounts of $UF_6$ frozen in the pin, the pin is kept at cold at approximately −36° C. and there is little opportunity for contamination. At −36° C., the pressure of $UF_6$ saturated vapor is very low, about 0.6 Torr.

$UF_6$ Sampling

The invention uses a vacuum-gas bench made of stainless steel incorporating gas check valves of the DU-4 and DU-10 types, needle inlet valves, a receiver, a system of uranium hexafluoride in-letting and discharging, vessels for storage of the gas under analysis, molecular fluorine and inert gases, lime chemical absorber, pressure transducers, and optical cells. All of the sealings of the valves and other components of the bench are made of Teflon because of the high reactivity of $UF_6$. Specifically, $UF_6$ reacts with the interior surfaces of the bench, the connecting pipelines and the optical cells. To prevent this interaction, the said elements of the system should be thoroughly passivated with molecular fluorine and with the gas to be analyzed at a pressure of 50-70 Torr. The passivation period is optimally 6-7 days. In the intervals between measurements the bench should be under a $UF_6$ pressure of 1-3 Torr. Before starting each measurement, a $UF_6$ sample should be, as a rule, additionally purified by means of serial operations of freezing, pumping-out and defrosting. The gas pressure in the bench, including the pressure in the receiver, and in the cell may be simultaneously monitored by differential pressure gages DP-5 and manometers of the VDG type. The additional error from the gages and the manometers should be eliminated immediately prior to taking measurements at the pressure of approximately equal to $10^{-2}$ Torr. These errors to the readings may be corrected with reference to the indications of the manometric lamp. All the measurements should optimally be taken at the ambient temperature of 23° C. and relative humidity of 80%.

With reference to FIG. 2, in one embodiment, the analytical cells or channels 103, 104, and 106 are made of stainless steel with polished interior walls. The optical length of these cells is 100 mm. In one embodiment of these cells, plates of barium difluoride, 40 mm in diameter, are used as cell windows. These windows are sealed with viton placed into special Teflon pockets to minimize the viton interaction with uranium hexafluoride. The cell is equipped with a mechanism for prompt congelation and removal of a sample from the cell.

Signal Recording and Processing

Referring to FIG. 2, in one embodiment, the signal processing board 113 is the multifunction National Instruments DAC/ADC board PCI-MIO-16E-1. The signal processing board 113 may be used for controlling the pumping of the diode laser 100, the thermal stabilizer 101, and the laser current supply 102. The signal processing board 113 may also be used for signal recording and processing. In one embodiment, the sampling frequency in the gas analyzer is about 250 KHz; the length of the sampling array is varied from 800 to 1200 points. In one embodiment, the data may be averaged from 1 to 255 times. The signal-to-noise ratio at the signal processing board 113 is about $1-2 \times 10^4$.

Figure 4:
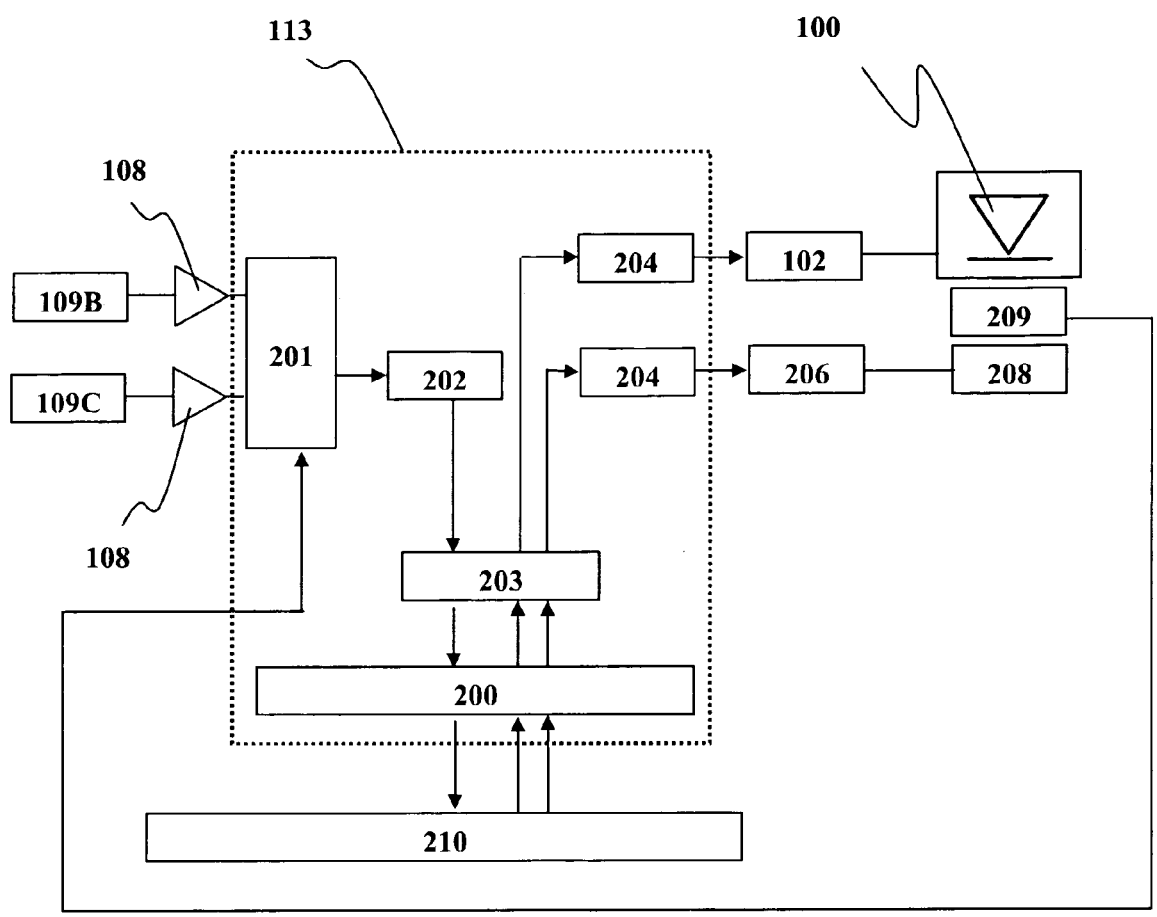
FIG. 4 is a schematic block diagram of the electric scheme of the gas analyzer.

FIG. 4 is a schematic representation of the equipment used to process the electric signals. Referring to FIG. 2 and FIG. 4, the electric signals are processed in the following way. The signals from the photo diodes 109A, 109B and 109C are amplified by the preamplifiers 108 before passing into a multiplexor 201. The electric signals are then passed through an analog-to-digital converter 202 before being placed into a buffer memory 203. The digitized signals are passed through a computer PCI bus 200 into a software program 210. After the software 210 performs process control and other calculations, the software 210 passes digital signals to digital-to-analog converters 204.

Referring to FIG. 4, one signal from the software 210 is passed to the DL power-supply 102. The DL current power-supply 102 provides excitation circuit pulses for the DL 100 used to measure the $UF_6$ sample.

Figure 6:
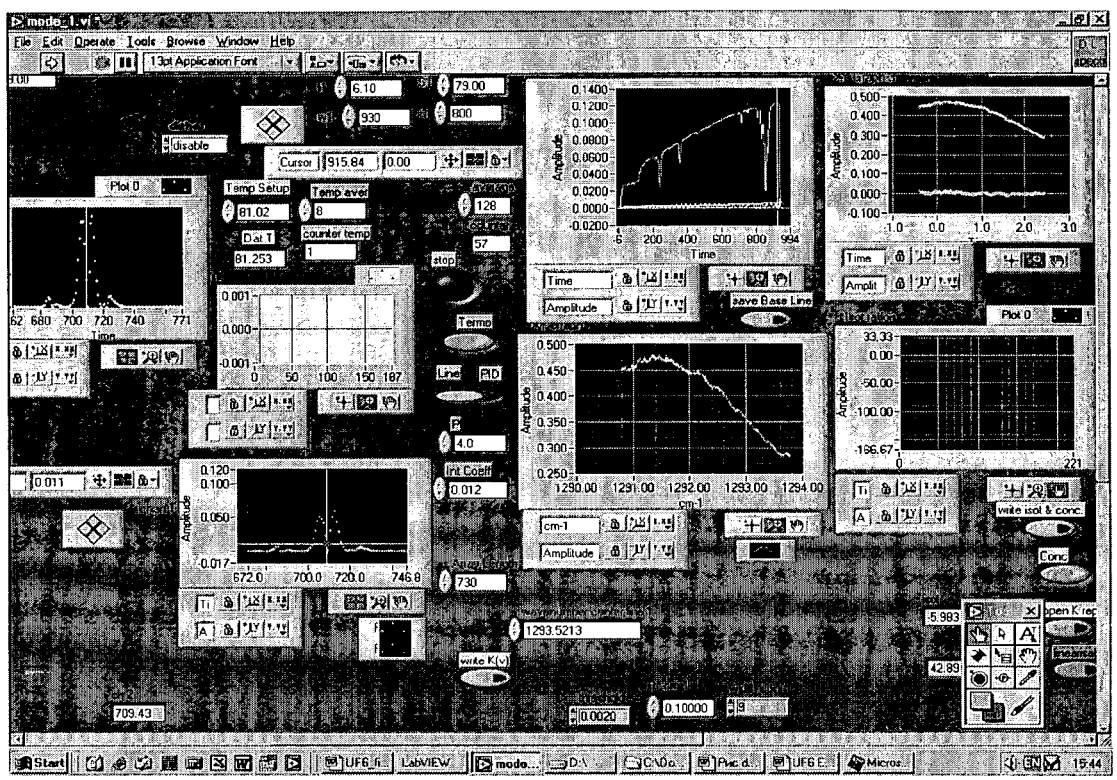
FIG. 6 is a view of one embodiment of the software interface to the gas analyzer.

Software is used to control the gas analyzer and to record and process the signals from the instruments. In one embodiment of the invention the software program uses the drivers manufactured by National Instruments and uses the software package NI LabView 6.0. In one embodiment, the software provides at least one graphical representation of the absorption spectrum of a gas sample containing $UF_6$. FIG. 6 shows one embodiment of the software display showing several graphs and several control elements.

Figure 5:
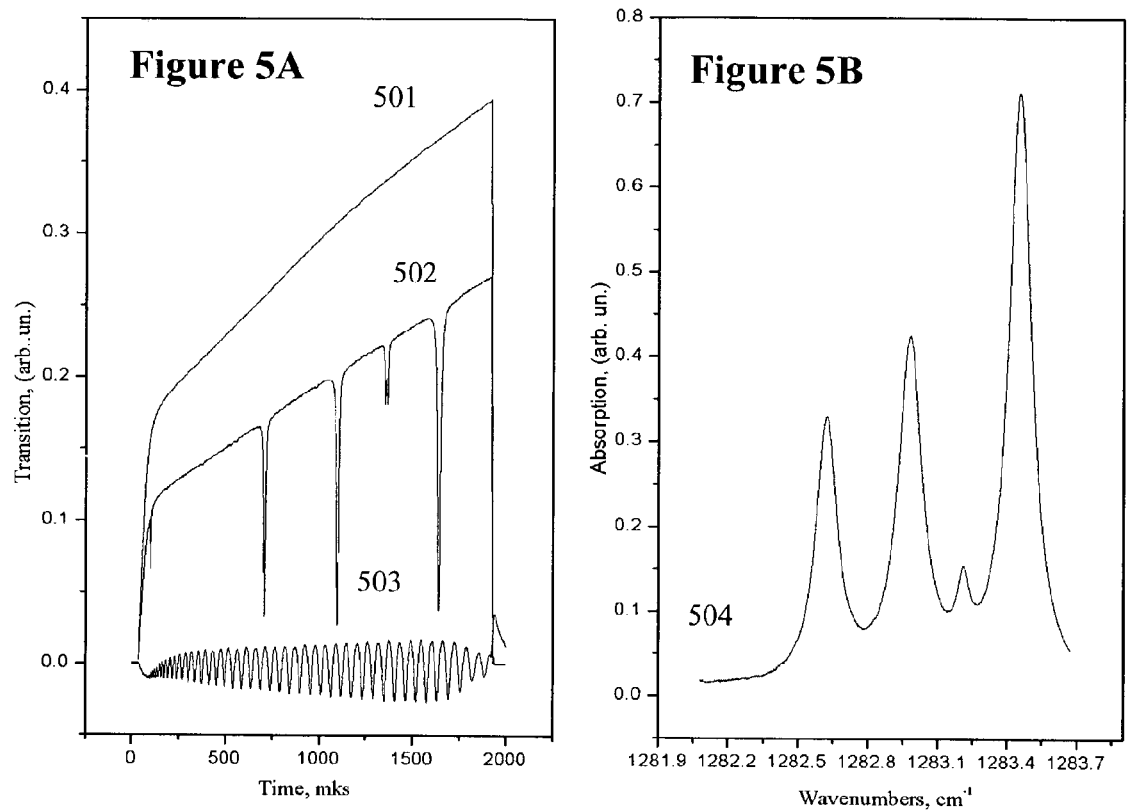
FIG. 5 is actually two graphs, FIG. 5A and FIG. 5B.

One of the main advantages of the DL gas analyzer is its three-channel system of spectra recording. FIG. 2 shows the three channels 103, 104 and 106 of the system. FIG. 5A shows a transmission signal 501 from an empty cell in the analytical channel 104, a transmission signal 502 from a methane gas (pressure P=1.5 Torr, cell length L=5 cm) in a calibration channel 103, and a transmission signal 503 from a Fabry-Perot interferometer in a calibration channel 106.

FIG. 5B presents an absorption spectrum of methane mixture in air 504 where the cell 104, from FIG. 2 has a length of 5 cm, the methane partial pressure is 20 Torr, and the total pressure of the sample in the cell is 1 atm.

TABLE 1

Parameters for the Three-Channel Diode Laser Gas Analyzer

| Parameter | Value |
|---|---|
| Wavelength, μ | 7.68 |
| Power, mW | 0.3 |
| Excitation current pulse duration, ms | 4-10 |
| Pulses repetition frequency, Hz | 40 |
| Total DL frequency tuning, $cM^{-1}$ | 80 |
| Continuous DL frequency tuning, $cM^{-1}$ | 2-3.5 |
| S/N | 10,000 |
| Spectral resolution, $cM^{-1}$ | 0.0002 |

Analysis of $UF_6$ Spectra

In one embodiment, the absorption spectra of $UF_6$ are measured with one of two models of Fourier Transform Spectrometers: Vector 22 and Bruker 66v. Both of these spectrometers are made by Bruker Optics, Inc. The Vector 22 model has a spectral resolution of 0.75 $cm^{-1}$, the Bruker 66v has a resolution of 0.2 $cm^{-1}$. The frequency scale of the spectrometer should be calibrated by the absorption spectra of $CH_4$ and $C_2H_2$ within the spectral range of interest. These absorption spectra may be found in the spectral database HITRAN.

With reference to FIG. 2, prior to a measurement of the $UF_6$ spectra, $UF_6$ gas should be frozen on the cold pin of the analytic cell 104. It is important that the end of the cold pin be placed into liquid nitrogen. The optimal time to freeze a sample is about 2 hours. Before the measurement, the $I_{cn}$-spectrum should be recorded. After the sample is frozen, the cell with the cold pin kept in liquid nitrogen may be placed into the spectrometer. The 10 spectrum at time=0, should be recorded. At time zero, there should be no gaseous $UF_6$ in the analytic cell 104.

Subsequently, the liquid nitrogen should be removed from the sample in the cell 104. The pin is heated by ambient air with a consequent evaporation of the substance under analysis and the sequence of spectra $I_i$ over time may be recorded. The time interval between the recording of successive spectra is optimally $\Delta t = t_i - t_{i-1} = 2$ min.

Figures 7, 7A, 7B:
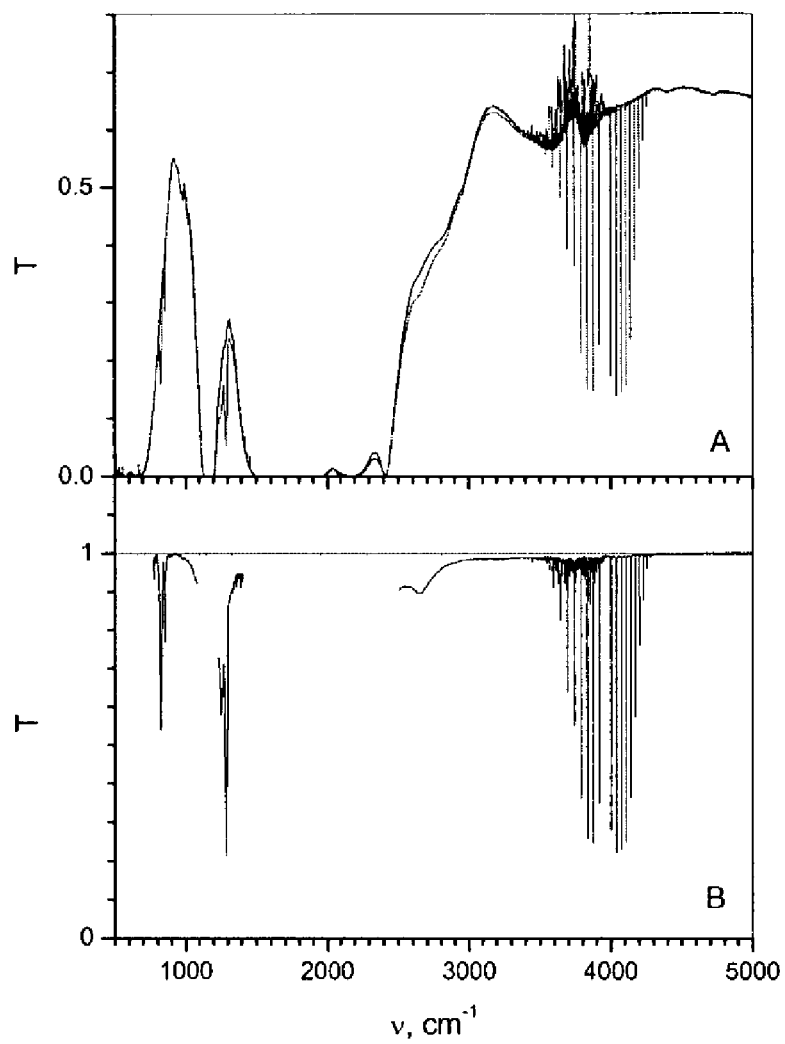
FIG. 7 is a graph of the transmission spectra of a sample cell containing uranium hexafluoride.

FIG. 7A is a graphical representation of the analytic cell 104 transmission spectra $I_i/I_{cn}$ for two instances of time, i=0 and i=31. At time zero, i=0, practically all of the cell 104 contents are frozen and thus there is practically no presence of the uranium hexafluoride gas in the sample cell 104. After 62 minutes, i=31, the pressure of uranium hexafluoride in the cell 104 is close to that of its saturated vapor pressure at ambient temperature. The following can be concluded from an analysis of the transmission spectra from FIG. 7A:

1. The decay of the transmission in the long waves band of the spectrum is dependent on the transmission of the cell windows knowing that $BaF_2$ is not transparent for $v<700\,cm^{-1}$.
2. The spectrum has two ranges, 1080 to 1230 $cm^{-1}$ and 1410 to 2500 $cm^{-1}$, in which the cell is nontransparent due to the absorption of nonvolatile products remaining from the passivation process that are deposited on the cell windows.

Thus, the equipment allows three spectral regions that are free from interference: 766-1080 $cm^{-1}$, 1230-1410 $cm^{-1}$ and frequencies over 2500 $cm^{-1}$. These regions may be used to analyze a sample in a cell 104. These regions are the ranges of interest for this invention.

FIG. 7B shows the spectrum of the cell transmission $T_{31}=I_{31}/I_0$ within the above mentioned spectral ranges. The transmission spectrum of the analysed gas mixture $T(v)$ can be represented as follows:

$$T_i(v) = \frac{I_i}{I_0} = \exp[-A(v)] = \exp[-\sigma(v)PL], \quad \text{Equation 1}$$

where $A(v)$ is the absorption spectrum of the gas under analysis; $\sigma(v)$ is the absorption cross section spectrum; P is its partial pressure, and L is the cell length.

Referring to FIG. 7B, the least informative spectral region is $v>2500\,cm^{-1}$ where noticeable absorption is due to HF (3600-4300 $cm^{-1}$) available in the analytic cell 104. Within this range there is a rather broad absorption band near 2700 $cm^{-1}$.

Referring to FIG. 7B, the range of 1200-1400 $cm^{-1}$ contains two narrow and partially overlapping bands with maxima at 1291 and 1254 $cm^{-1}$. The range of 700-1100 $cm^{-1}$ contains two narrow absorption bands with maxima at 821 and 852 $cm^{-1}$.

The absorption spectra for $UF_6$ are presented in an article appearing in the Journal of Chemical Physics in 1974 by R. S. McDowell. This article is subsequently referred to as Reference 1. The full reference to this article is: R. S. McDowell, L. B. Asprey, R. T. Paine, "Vibrational spectrum and force field of uranium hexafluoride," J. of Chemical Physics, Vol. 61, No. 9, 1974. From this article, the $UF_6$ molecule has six normal vibrational modes, i.e. $v_1=667\,cm^{-1}$, $v_2=534\,cm^{-1}$, $v_3=626\,cm^{-1}$, $v_4=186\,cm^{-1}$, $v_5=200\,cm^{-1}$, and $v_6=143\,cm^{-1}$. None of the fundamentals related to the above vibrational modes are observable in the spectral range of interest. The regions of interest contain the combination absorption bands of the $UF_6$ molecule as specified in Table 2.

The first column of Table 2 identifies a corresponding absorption band, the second column identifies the frequency related to the band maximum, and the third column shows the absorption cross section $\sigma$ at the band maximum. Table 3 presents the isotope shifts for some normal vibrational modes of uranium hexafluoride that are of the most interest.

TABLE 2

$UF_6$ Absorption Bands

| Assignment | v, $cm^{-1}$ | $\sigma$, $cm^{-1}$/atm |
|---|---|---|
| $2v_3 + v_6$ | 1386 ± 2 | 0.00175 |
| $v_1 + v_2 + v_6$ | 1341 | 0.00875 |
| $v_1 + v_3$ | 1290.9 ± 0.5 | 0.717 |
| $v_2 + v_6$ | 1211 ± 2 | 0.0007 |
| $v_2 + v_3$ | 1156.9 ± 0.5 | 0.822 |

TABLE 2-continued

UF$_6$ Absorption Bands

| Assignment | v, cm$^{-1}$ | σ, cm$^{-1}$/atm |
|---|---|---|
| v$_3$ + 2v$_6$ | 905 ± 2 | 0.0035 |
| v$_1$ + v$_4$ | 852.8 ± 0.5 | 0.122 |
| v$_3$ + v$_5$ | 821 | 0.332 |

TABLE 3

UF$_6$ Isotope Shifts

| Isotope Shifts, cm$^{-1}$ | $^{235}$UF$_6$-$^{238}$UF$_6$ |
|---|---|
| v$_1$ | 0 |
| v$_3$ | 0.65 ± 0.09 |
| v$_4$ | 0.16 ± 0.09 |

Figure 8:
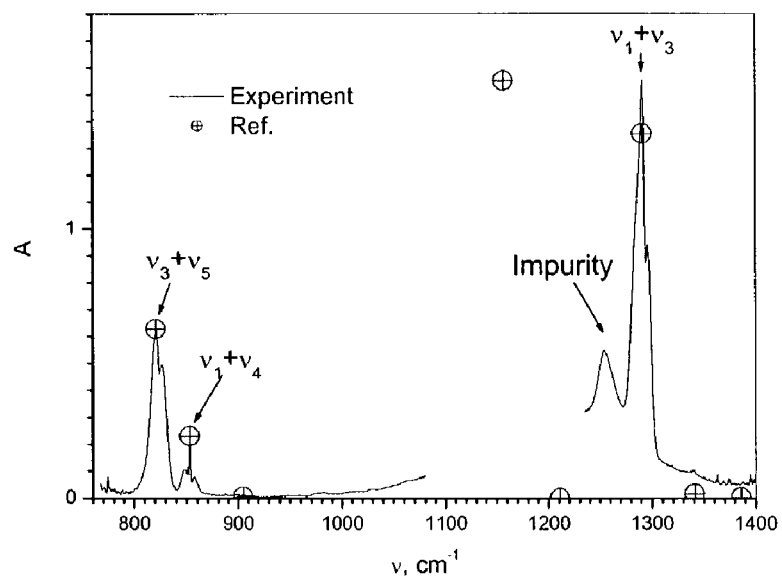
FIG. 8 is a graph of the absorption spectrum of a gas sample containing uranium hexafluoride.

The absorption spectrum of a sample gas mixture, shown in FIG. 8, may be generated by using the data presented in FIG. 7B and Equation 1. In FIG. 8, markers, represented by the symbol of a circle with a cross in it, indicate the positions of the absorption of band maxima according to the information presented in Table 2. Referring to Table 2, three of the combination bands of the UF$_6$ molecule may be observed: v$_3$+v$_5$, v$_1$+v$_4$ and v$_1$+v$_3$. The remaining two bands mentioned above are related to gaseous impurities in the cell.

The remainder of the invention uses a diode laser emitting near 1300 cm$^{-1}$, i.e., within the range containing the UF$_6$ combination band v$_1$+v$_3$; this combination band has a large isotope shift. The accuracy of the measurements presented by R. S. McDowell in his journal article (mentioned above) is insufficient to distinguish the two isotopes of uranium because the error of determining the maximum of the v$_1$+v$_3$ band of UF$_6$ is 0.5 cm$^{-1}$, on the same order of magnitude as the isotope shift shown in Table 2. Referring to FIG. 8, the v$_1$+v$_3$ band is overlapped by an absorption by the impurity molecule. In determining the isotopic composition of uranium hexafluoride, the absorption of the impurity must be taken into account.

Analysis of UF$_6$ Spectra Over Time

Figure 9:
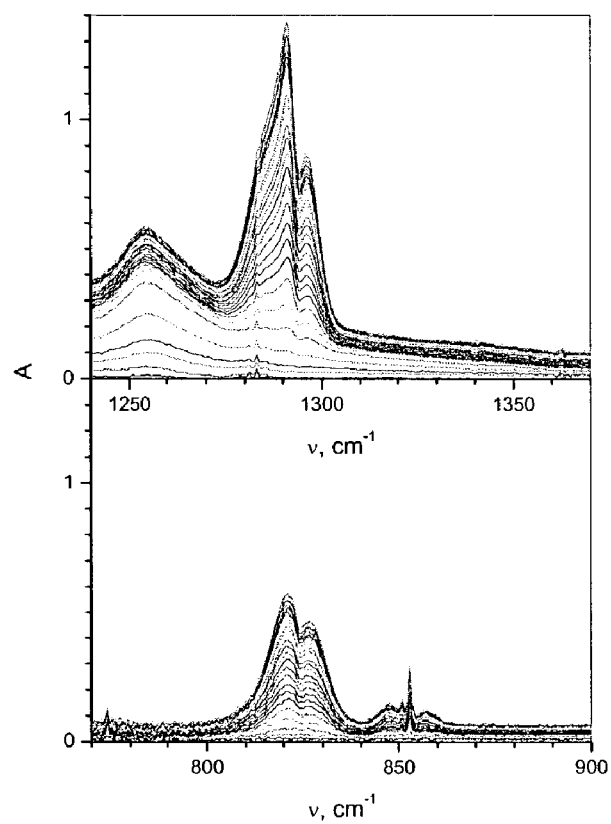
FIG. 9 is a graph of the absorption spectra over time of a gas sample containing uranium hexafluoride.

It is important to note the time dependencies of the components of gas mixture in the analytic cell 101. Measurements of a gas sample may be taken at any time interval. FIG. 9 shows the evolution of absorption spectra A(v) in the vicinity of UF$_6$ absorption bands over time. In FIG. 9, the spectra of UF$_6$ are recorded at intervals of 2 minutes as the cold pin is heated by the ambient air. The analogous absorption spectra of HF are also recorded. In FIG. 9, the impurity molecule absorption becomes evident as the UF$_6$ absorption just becomes observable. In FIG. 9, the impurity absorbs at a frequency between 1250 and 1260 cm$^{-1}$.

The HF concentration can be determined at each instant of time by reference to the HITRAN database and the transmission spectra from the sample. The linear dependence between the integral absorption and molecular concentration of HF can be taken into account by noting the significant difference between the Doppler line width (0.005 cm$^{-1}$) and the spectrometer resolution (0.75 cm$^{-1}$) where the concentration is evaluated by the spectral lines and where with the absorption is less than 3%.

Figure 10:
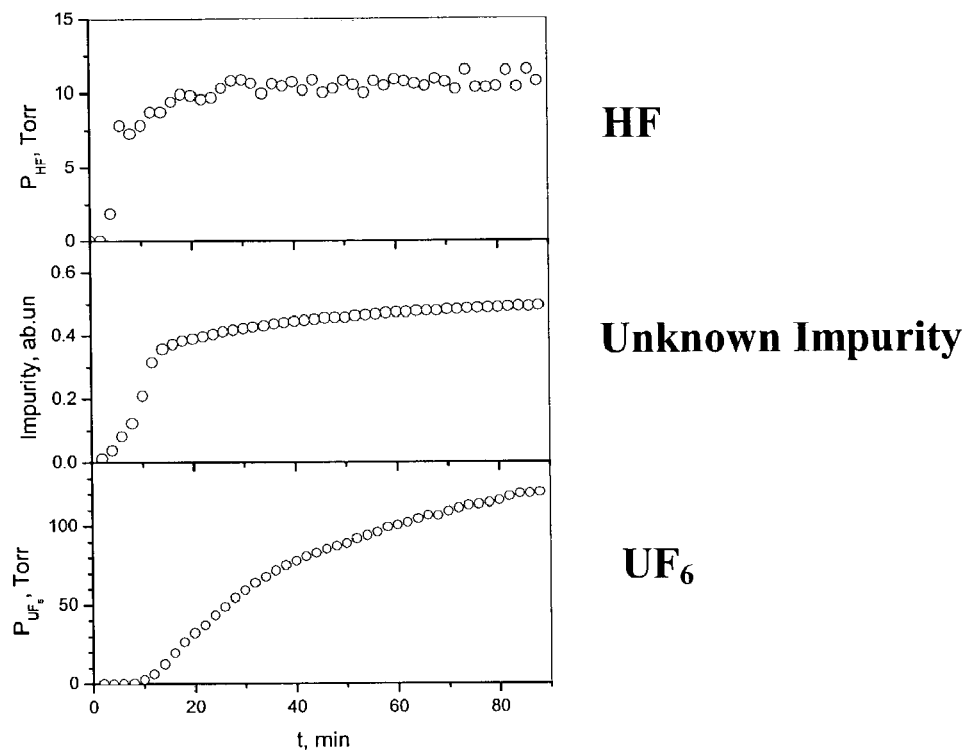
FIG. 10 is a graph of the time dependence of the concentration of HF, the unknown impurity, and $UF_6$.

The top plot in FIG. 10 presents the HF concentration over time in the sample cell as the cold pin is heated and the partial pressure of HF increases. Gaseous HF is observed after just a few minutes of heating, its partial pressure quickly rises to about 10 Torr. The middle plot of FIG. 10 shows the presence of the unknown impurity over time; the unknown impurity absorbs at a frequency band centered around 1254 cm$^{-1}$. This impurity evaporates later than HF and fully evaporates by the tenth minute. Its partial pressure can be estimated as 3-30 Torr subject to the typical absorption cross sections of the fundamental bands of molecules. The UF$_6$ concentration is evaluated free from the interference of the unknown impurity by the band v$_3$+v$_5$=821 cm$^{-1}$ with reference to Table 2. The UF$_6$ concentration over time is presented in the bottom plot of FIG. 10. The presence of UF$_6$ gas is detectable by the tenth minute of heating and its concentration increases over the whole sample measurement. The concentration of UF$_6$ gas asymptotically approaches the value of the saturated vapor pressure of uranium hexafluoride at ambient temperature. The slight increase in the molecular concentrations of the unknown impurity and HF gases after the tenth minute, as shown in the two upper plots of FIG. 10, is caused by the evaporating UF$_6$ that pushes these two other gases into the optical path of the spectrometer.

Figure 11:
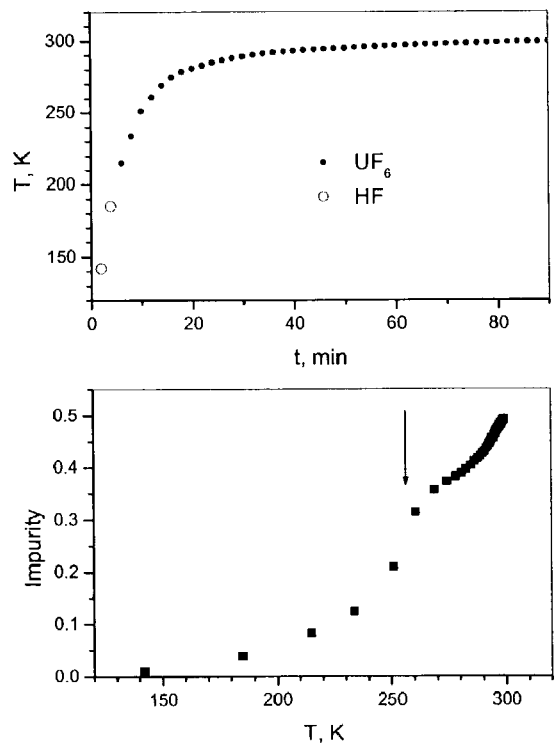
FIG. 11 is a graph of the time dependence of the temperature in the cold part of the analytic cell and a graph of the temperature dependence of the unknown impurity.

The top plot of FIG. 11 represents the temperature of the sample over time as taken from the measurements of UF$_6$ and HF over time and knowing the relationship between the UF$_6$ and HF saturated vapor pressure and temperature. The bottom plot of FIG. 11 represents the temperature dependence of the unknown impurity. The unknown impurity can be identified by noting that it has a saturated vapour pressure of 3-20 Torr at 260 K, and has characteristic 10 absorption bands (shown in FIG. 8).

Figure 12:
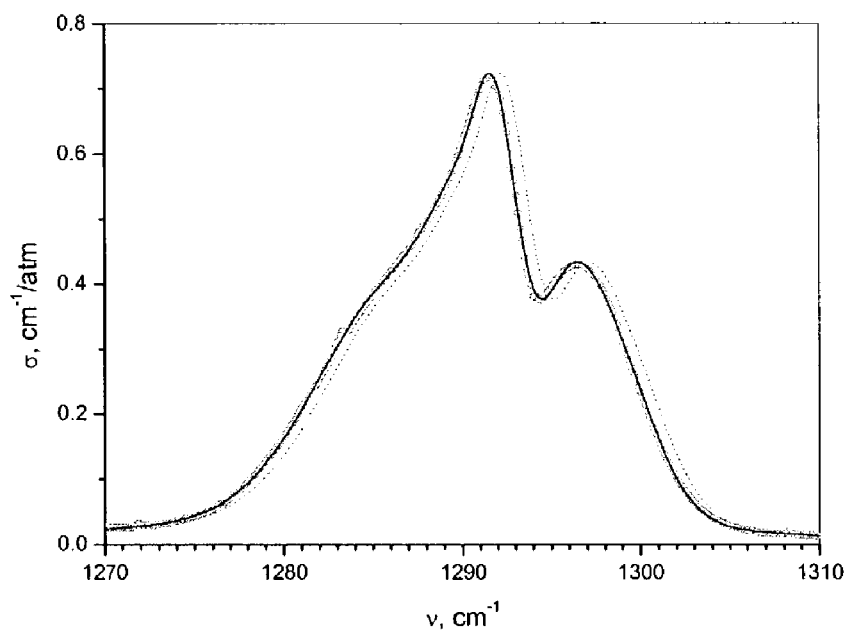
FIG. 12 is a graph showing the plot of three values: the absorption spectrum of a gas sample containing uranium hexafluoride, a calculated model spectrum of $^{238}UF_6$, and a calculated model spectrum of $^{235}UF_6$.
Figure 13:
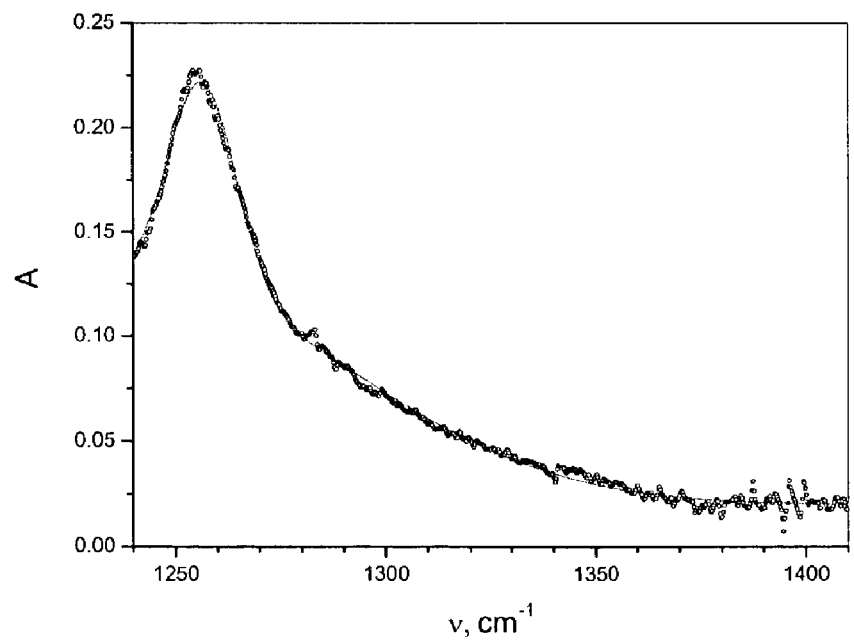
FIG. 13 is a graph showing the absorption spectrum and model spectrum of the unknown impurity.

Using the data presented in FIG. 9, the absorption spectra of UF$_6$ and the unknown impurity can be isolated. The absorption spectrum for UF$_6$ is shown in FIG. 12, the absorption spectrum of the unknown impurity is shown in FIG. 13. The shape of the absorption cross section of uranium hexafluoride can be determined using the experimental absorption spectra. According to the authors of Reference 1, the absorption cross section measurement are only accurate to within 10%.

Using the current invention, this same cross sectional measurement and calibration are accurate up to 0.03 cm$^{-1}$ subject to the resolution of the Fourier Transform Spectrometer and the method of its calibration (see above). To obtain this improved accuracy, it is necessary to record and plot the absorption spectra of both $^{238}$UF$_6$ and $^{235}$UF$_6$. The accuracy of the frequency calibration of those spectra depends on the isotope shift of band v$_1$+v$_3$–0.65 cm$^{-1}$ (see Table 2) and on the accuracy of determining the UF$_6$ isotopic composition. In order to measure the $^{235}$UF$_6$ concentration to within a 1% accuracy, all the spectra should be measured to within a frequency resolution of 0.0065 cm$^{-1}$. Such high resolution requires the use of a Fourier Transform Spectrometers such as a Bruker HR 120 or Bomem. In order to evaluate the $^{235}$UF$_6$ concentration up to 0.1% accuracy, it is required to resolve the frequency to within 0.00065 cm$^{-1}$, which at present can be achieved only by using tunable diode lasers. In this invention, the frequency scale accuracy is up to 0.0002 cm$^{-1}$ (see above), which is equivalent to the accuracy of determining the isotopic composition of uranium hexafluoride up to 0.03%.

The absolute value of the UF$_6$ absorption cross section given in FIG. 13 affects the accuracy of determining the UF$_6$ partial pressure while causing no loss of accuracy in evaluating the UF$_6$ isotopic composition. The UF$_6$ absorption cross section spectrum can be obtained from a sample containing a presumably natural isotopic composition of UF$_6$.

Experimental data similar to that presented in FIG. 12 may be used to construct a model spectrum of the UF$_6$ absorption cross section; this model is shown as a solid curve in FIG. 12.

The superposition of six Gaussians reproduces the model spectrum to within the experimental accuracy. The model spectrum is indicative of $^{238}UF_6$. The model spectrum of $^{235}UF_6$ can be constructed in a similar fashion noting that any variations of the atomic mass of the $UF_6$ molecule is likely to produce negligiable changes in both the molecule rotational value and the Coriolis constant because of the relatively low change in the mass. Therefore, any changes in the shape of the $UF_6$ spectrum for various isotopes can be ignored. Subject to this assumption, the $^{235}UF_6$ model spectrum is shifted to a higher frequency by 0.65 cm$^{-1}$ relative to the model spectrum of $^{238}UF_6$, shown as a dotted line in FIG. 12.

The spectrum of the unknown impurity is shown in FIG. 13: the actual recorded data are represented by circles, the model is represented by the solid line. The model fits the data with sufficient accuracy with the use of three Lorentzians. One of the keys to this invention is the construction and fit of the analytical models of $UF_6$ and the unknown impurity to the recorded spectra. Subject to the higher accuracy of the above models the isotopic composition of uranium hexafluoride can be determined with a high degree of accuracy.

Algorithm to Determine the Isotopic Composition of Uranium Hexafluoride

The isotopic composition of uranium hexafluoride can be measured using a tunable diode laser (DL) operating within the region of the Q-branch of the $UF_6 v_1+v_3$ band. The method of the frequency scale calibration is described above, its accuracy is evaluated below. The DL should provide an uninterrupted emitting frequency of about 3 cm$^{-1}$ in the vicinity of the absorption maximum of the uranium hexafluoride Q-branch.

Figure 14:
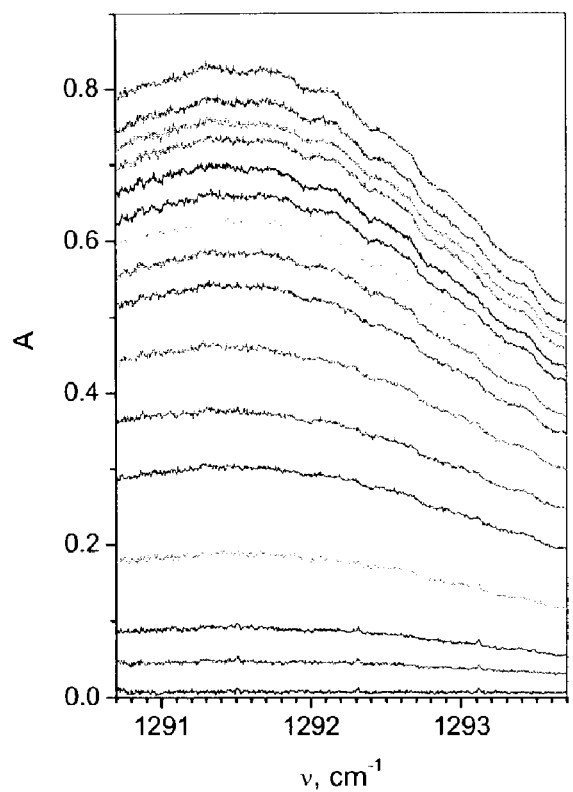
FIG. 14 is a graph showing the evolution of the absorption spectrum of a uranium hexafluoride sample in the course of heating the cold ping inside the analytic cell.

FIG. 14 shows the evolution of the absorption spectra of the uranium hexafluoride sample as measured by the diode laser when the cold pin containing the $UF_6$ is heated. At time=0, the contents of the cell as a whole are frozen in the cold pin because the pin is in liquid nitrogen. At that moment the reference signal $I_o$ from Equation 1 should be recorded. FIG. 14 presents the spectra absorption of the various gaseous components as the sample evaporates. As seen in FIG. 14, at first rather narrow lines are observed. At a certain time, with reference to FIG. 10, HF begins to evaporate. According to an article published by Rothman, et al., in 1998, (L. S. Rothman, et al., JQSRT, 60, 665-710 (1998)), the HF molecule does not have absorption within the specified spectral range. Apparently, the observed spectral bands belong to the dimer HF-HF. As the cold pin is heated, $UF_6$ and the unknown impurity start to evaporate. The fine spectral structure related to the $UF_6$ absorption in FIG. 14 is significant. Though the structure is not prominent to the untrained eye, the isotopic composition of $UF_6$ can be measured and determined with a high degree of accuracy with this invention.

Ignoring the fine structure shown in FIG. 14, a simple model can be used. Subject to the model spectra described above, within a specified spectral range, the absorption spectrum of the analyzed hexafluoride gas mixture in the $v_1+v_3$ band can be represented as follows:

$$A = PL\sigma_o \left[1 - \frac{2(v-v_0)^2}{\omega^2}\right] + A_{impurity}[1 + a(v-1292)] \quad \text{Equation 2}$$

where $\sigma_0$ is as given in Table 2, L is the cell length, P is the partial pressure of $UF_6$, $A_{impurity}$ is the absorption of an unknown impurity, values $\omega$ and $\alpha$ are determined by the model spectra of uranium hexafluoride and the unknown impurity described above, and value $v_0$ represents a possible change in the $UF_6$ isotopic composition. The values $\omega$ and $\alpha$ are evaluated within a specific spectral range using the model spectra described above. Subject to Equation 2 and actual data, the $UF_6$ partial pressure and the unknown impurity content can be determined independently.

Figure 15:
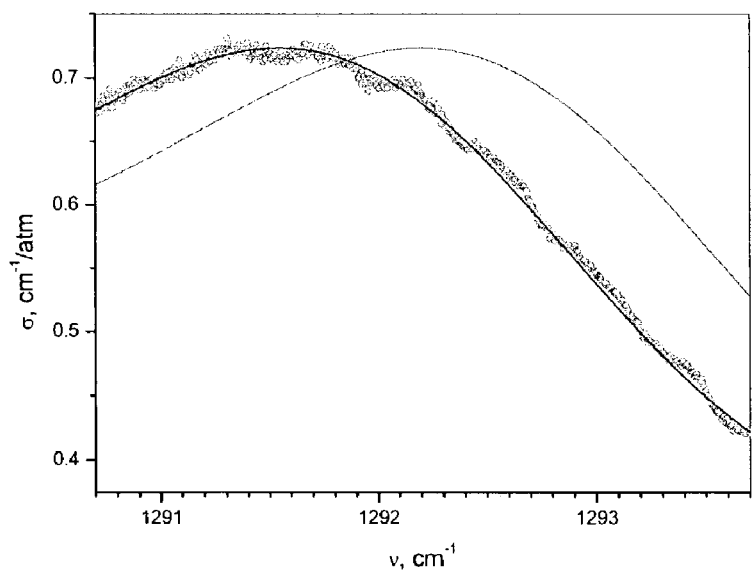
FIG. 15 is a graph showing the uranium hexafluoride absorption spectrum and the model spectra of $^{238}UF_6$ and $^{235}UF_6$.

FIG. 15 shows one recorded absorption spectra of a sample of $UF_6$ gas. The absorption coefficient was evaluated according to the procedure mentioned above. The solid curve represents the model spectrum of $^{238}UF_6$, the dotted curve that of $^{235}UF_6$. Assuming that the $^{235}UF_6$ concentration in the mixture analysed is I, one can transform Equation 2 as follows:

$$A = PL\sigma_o \left\{(1-I)\left[1 - \frac{2(v-v_{238})^2}{\omega^2}\right] + I\left[1 - \frac{2(v-v_{235})^2}{\omega^2}\right]\right\} + A_{impurity}[1 + a(v-1292)] \quad \text{Equation 3}$$

where $v_{238}$ and $v_{235}$ are the positions of the absorption bands maxima of the two isotopic modifications of uranium hexafluoride. In Equation 2 and Equation 3, the spectrum of $UF_6$ at the absorption maximum is given up to the square (quadratic) term of the polynomial expansion. The real processing algorithms take account of the higher orders of absorption spectra expansion in the vicinity of the absorption maximum, i.e. up to the 5th order.

If the partial pressure of uranium hexafluoride and that of an unknown impurity are determined during the preliminary processing, the following value can be estimated as follows:

$$\Delta A = A - A_{impurity} - PL\sigma_{238} = PLI(\sigma_{235} - \sigma_{238}) \quad \text{Equation 4}$$

The uranium isotopic composition in the gas mixture can be determined as the correlation between value $\Delta A$, from Equation 4, and the value estimated by the model spectra $(\sigma_{235}-\sigma_{238})$.

Figure 16:
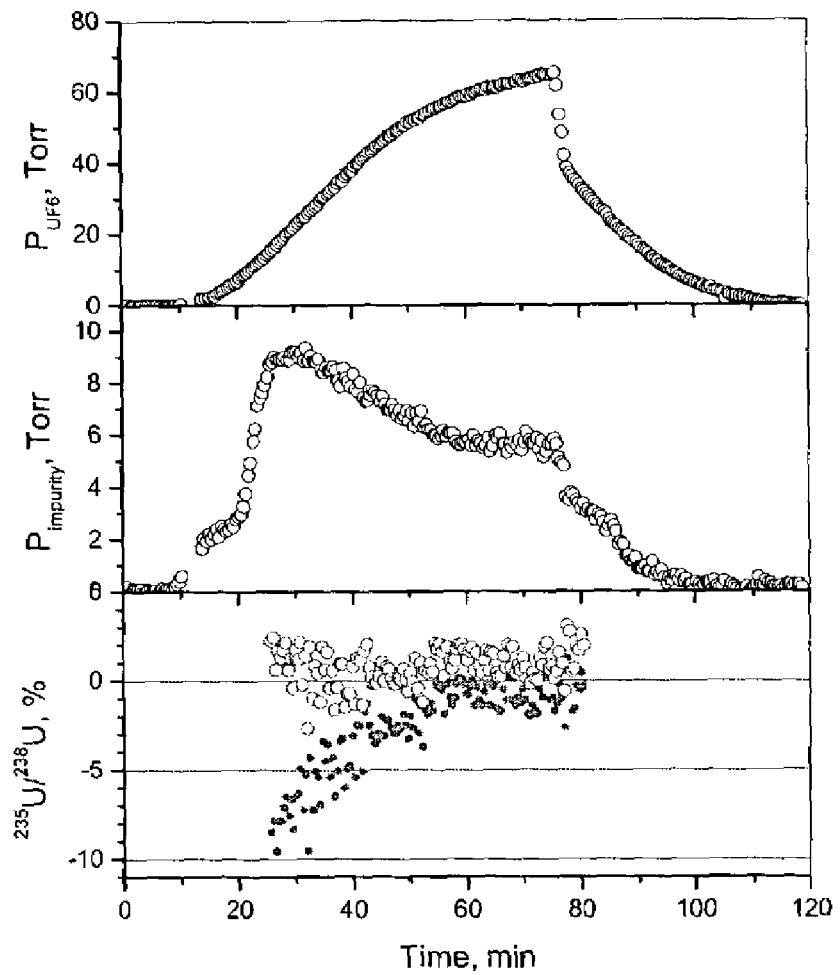
FIG. 16 is a graph showing three important time dependencies: the partial pressure of uranium hexafluoride, the absorption of the unknown impurity, and the isotopic composition taking into account the presence of the unknown impurity.

FIG. 16 presents the results of the above mentioned procedure. The top plot of FIG. 16 (FIG. 16A) shows the time variation of the $UF_6$ partial pressure. The middle plot of FIG. 16 (FIG. 16B) shows the content or partial pressure of the unknown impurity. The data shown are comparable with those given in FIG. 10. The difference in the behaviour of the unknown impurity may be attributed to various positions of optical beams relative to a cell optical axis in these two measurements (see above). In the first case, evaporating $UF_6$ pushed the unknown molecule into the region of measurement while in the second case, the evaporating $UF_6$ pushed the unknown molecule out of the region of measurement. Subject to that observation, the data presented in both FIG. 10 and FIG. 16 are in agreement. The bottom plot in FIG. 16 (FIG. 16C) shows the uranium isotopes ratio (solid circles) in the gas mixture over time. In this invention, an unknown impurity and its spectrum are of critical importance because if they are ignored, the error of measuring the $^{235}UF_6$ content may be up to 10%, shown as the open circles in FIG. 16C.

The random error in the content of isotope $^{235}U$ is characterized by a root-mean-square spread of about 1%. The data shown in this disclosure demonstrate a drift in the measured values. In one embodiment of the invention, the $UF_6$ pressure can be increased very slowly by very slowly changing the trap temperature accounting. This slow change can account for the drift in the measured values. However, in another embodiment of the invention, the sample gas can be pumped in quickly and the measured values do not show such a drift. The second embodiment can provide a root-mean-square error of 0.27%.

In short, the invention measures the isotopic composition of gaseous $UF_6$ with an error of 0.27%. Referring to FIG. 2, the limiting component in the accuracy of the measurement is the noise from the photodiodes 109. In one embodiment, the accuracy of measuring the isotopic composition of uranium hexafluoride is improved by at least by an order of magnitude when the photoreceiver or photo diode 109 is replaced with a higher quality one than the one used to practice this invention.

CONCLUSION

Equipment and software are used to measure the isotope ratio of low-pressure gaseous $UF_6$ to a high precision, the ratio of $^{235}UF_6$ to $^{238}UF_6$. The measurement uses tunable diode laser spectroscopy. In one embodiment, a three-channel diode laser analyzer operates at the wavelength 7.68 μm., which is most suitable for gaseous $UF_6$ in the combination band $v_1+v_3$. The scientific model to determine this measurement is given. The invention is suitable for the measurement of real gas mixtures. Error sources in the measurement are identified and presented. The precision of the measurement of isotope $^{235}U$ is characterized by a root-mean-square error of about 0.27%, a dramatic improvement over the prior art accuracy of 10%. The accuracy for long-term measurements, such more than one hour, is about 1% error. The error in the method can be reduced by at least one order of magnitude by making substitutions of more sensitive, currently available instruments and components.

What is claimed is:

1. An apparatus for determining the relative amounts of uranium isotopes in uranium hexafluoride gas comprising:
    a thermally stabilized tunable diode laser, wherein the diode laser emits a laser radiation wherein the laser radiation is split into a first beam, a second beam, and a third beam;
    a sample channel wherein the first beam of laser radiation is directed through said sample channel containing a sample gas to be received by a first photodetector;
    a first calibration channel wherein the second beam of laser radiation is directed through said first calibration channel containing a calibration reference gas to be received by a second photodetector, wherein the reference gas is methane, acetylene, or a mixture of methane and acetylene;
    a second calibration channel wherein the third beam of laser radiation is directed through said second calibration channel to be received by a third photodetector;
    a signal processing circuit wherein the signal processing circuit receives a first output signal from the first photodetector and a second output signal from the second photodetector and a third output signal from the third photodetector;
    wherein the signal processing circuit calculates relative amounts of isotopes in the sample gas, wherein the signal processing circuit isolates the absorption spectrum of uranium hexafluoride from the absorption spectrum of any impurity and compares the uranium hexafluoride absorption spectrum of the sample gas to model absorption spectra of different uranium hexafluoride isotopes.

2. The apparatus of claim 1 wherein the first calibration channel is an absolute frequency calibration channel.

3. The apparatus of claim 1 wherein the second calibration channel is a relative frequency calibration channel.

4. The apparatus of claim 3 wherein the relative frequency calibration channel comprises a Fabry-Perot interferometer.

5. The apparatus of claim 1 wherein the signal processing circuit regulates the laser radiation emitted by the thermally stabilized tunable diode laser.

6. The apparatus of claim 1 wherein the laser radiation has a center wavelength of 7.68 μm.

7. The apparatus of claim 1 wherein the laser radiation has a mode length of 3 cm$^{-1}$.

8. A method for determining the relative amounts of the uranium isotopes in uranium hexafluoride gas comprising the steps of:
    emitting laser radiation through a first channel, a second channel, and a third channel with a thermally stabilized tunable diode laser;
    detecting an absorption spectrum of a sample of uranium hexafluoride gas contained within the first channel;
    detecting a first transmission of laser radiation through a calibration gas contained within the second channel, wherein said calibration gas is methane, acetylene, or a mixture of methane and acetylene;
    detecting a second transmission of laser radiation through an interferometer contained within the third channel;
    calibrating the output of the tunable diode laser using the detected first transmission of laser radiation and the second transmission of laser radiation; and
    determining the isotopic ratio of uranium isotopes in the sample of uranium hexafluoride gas by isolating the absorption spectrum of uranium hexafluoride from the absorption spectrum of any impurity and comparing the uranium hexafluoride absorption spectrum of the sample gas to model absorption spectra of different uranium hexafluoride isotopes.

9. The method of claim 8 wherein the interferometer contained within the third channel is a Fabry-Perot interferometer.

10. The method of claim 8 wherein the step of determining the isotopic ratio of uranium isotopes in the same of uranium hexafluoride gas further comprises the step of calculating an absorption cross-section of the uranium hexafluoride gas.

* * * * *

UNITED STATES PATENT AND TRADEMARK OFFICE
CERTIFICATE OF CORRECTION

PATENT NO. : 7,535,006 B2      Page 1 of 1
APPLICATION NO. : 10/457646
DATED : May 19, 2009
INVENTOR(S) : Nadezhdinskii et al.

It is certified that error appears in the above-identified patent and that said Letters Patent is hereby corrected as shown below:

In the Specification:

Column 7, line 52, please change [10] to -- $I_0$ -- to read "The $I_0$ spectrum at time = 0,".

Column 10, line 29, please delete "10" to read "and has characteristic absorption bands (shown in FIG. 8)."

Signed and Sealed this

Twenty-fifth Day of August, 2009

David J. Kappos
*Director of the United States Patent and Trademark Office*